United States Patent
Brekelmans et al.

(10) Patent No.: US 7,377,152 B2
(45) Date of Patent: May 27, 2008

(54) METHOD AND DEVICE FOR DETERMINING A CHARACTERISTIC VALUE THAT IS REPRESENTATIVE OF THE CONDITION OF A GAS

(75) Inventors: Kees C. J. M. N. Brekelmans, Veenendaal (NL); Jan Willem J. W. Van Rijswijk, Veenendaal (NL)

(73) Assignee: Brooks Instrument, LLC, Hatfield, PA (US)

( * ) Notice: Subject to any disclaimer, the term of this patent is extended or adjusted under 35 U.S.C. 154(b) by 0 days.

(21) Appl. No.: 10/531,845

(22) PCT Filed: Oct. 17, 2003

(86) PCT No.: PCT/EP03/11565

§ 371 (c)(1),
(2), (4) Date: Nov. 21, 2005

(87) PCT Pub. No.: WO2004/036209

PCT Pub. Date: Apr. 29, 2004

(65) Prior Publication Data

US 2006/0123892 A1    Jun. 15, 2006

(30) Foreign Application Priority Data

Oct. 18, 2002    (EP)    .................. 02023415

(51) Int. Cl.
*G01N 25/00*    (2006.01)
(52) U.S. Cl. .................. 73/61.76; 73/25.03; 702/100; 374/43

(58) Field of Classification Search ............... 73/61.76, 73/23.21, 25.03; 702/100; 374/43, 36
See application file for complete search history.

(56) References Cited

U.S. PATENT DOCUMENTS 3,393,562 A  *  7/1968  Breedlove .................... 374/37

(Continued)

FOREIGN PATENT DOCUMENTS

DE           4118781 A      12/1992

(Continued)

*Primary Examiner*—Hezron Williams
*Assistant Examiner*—Samir M. Shah
(74) *Attorney, Agent, or Firm*—Sonnenschein Nath & Rosenthal LLC (57) ABSTRACT

The invention relates to a device and methods for characterizating flowing substances, liquid or gas. The device includes: a transport duct with a heating or a cooling element; a temperature difference sensor having a temperature measurement cell downstream of the heating or cooling element and means to determine a temperature difference in the flowing substance upstream and downstream of the heating or cooling element; a flow control means having flow measurement means for measuring a mass flow characteristic and a flow correction means for correcting for measured mass flow variations; and an evaluation means for evaluating a characterizing feature of the flowing substance comprising a function relating temperature differences measured on one or more calibration substances to one or more characterizing features of the flowing substance. Various embodiments relate to the related use and methods of the device for identification and control of the flowing substance.

38 Claims, 3 Drawing Sheets

U.S. PATENT DOCUMENTS 5,167,450 A * 12/1992 Nukui et al. .................. 374/31
5,311,447 A * 5/1994 Bonne ........................ 702/50
6,425,281 B1 * 7/2002 Sheriff et al. ................ 73/23.2
2002/0141945 A1 * 10/2002 Foster et al. ................. 424/46
2004/0030522 A1 * 2/2004 Tison et al. ................. 702/100

FOREIGN PATENT DOCUMENTS

| | | |
|---|---|---|
| DE | 10122039 A | 11/2002 |
| EP | 0469649 A | 2/1992 |
| EP | 0554095 A | 8/1993 |
| EP | 0554095 A2 * | 8/1993 |
| EP | 0715169 A | 6/1996 |
| FR | 2818746 A | 6/2002 |
| WO | WO 9308457 A | 4/1993 |

* cited by examiner

METHOD AND DEVICE FOR DETERMINING A CHARACTERISTIC VALUE THAT IS REPRESENTATIVE OF THE CONDITION OF A GAS

This application is a 35 U.S.C. §371 application of WO 2004/036209, filed Oct. 17, 2003 claiming priority to EP Appl. No. 02023415.9 filed Oct. 18, 2002, both of which are incorporated herein by reference in their entirety.

BACKGROUND OF THE INVENTION

The invention relates to a device and methods for the characterisation of a flowing substance. Particular embodiments of the invention relate to the use of the device for the identification of a flowing substance, for controlling the flow of a fuel or combustion gas to deliver a controlled heat of combustion and for measuring the heat capacity of a gas. Further embodiments of the invention relate to a flow control device for controlling the flow rate of a flowing substance and a method for the combustion of a fuel or combustion gas.

Flow control devices are used to deliver a controlled amount of a flowing substance. This works well in most situations, where the nature of a flowing substance is known and substantially constant in composition over time. However, there are also situations where the nature of the flowing substance is not known and can vary in time. Such a situation occurs for example in natural gas distribution networks where different suppliers pump natural gas of different origin and/or composition into the network to various customers. The gas supplied to the customers can vary over time in composition and heat of combustion. The flow of the gas changes in an unknown way because of changes in the viscosity, the density or heat capacity of the various different gasses. In such a situation, most flow control devices, like thermal flow controllers, cannot deliver an accurately controlled mass flow. Because of these unknown changes in the mass flow and heat of combustion, problems can occur like the incomplete combustion of the gas, a too low energy recovery and emission problems.

Another example of such a situation, and a new application of the invention as described hereafter, is the distribution of fuels for engines. For optimum engine performance and fuel economy it is desirable that the flow control is able to deal with varying and/or unknown fuel types and compositions. This will become more and more relevant in view of the increasing desire to further optimise fuel economy, to minimise damaging exhaust gasses and in view of the expected increasing diversification in fuels. Hence, there is a desire for a device for the characterisation of the flowing substance.

Direct and accurate measurement of combustion energy is achieved by actually combusting the gas and measuring the heat. Well known devices for the combustionless characterisation of flowing substances, like chromatography or spectrometry, are accurate but have the disadvantages that they are difficult to integrate in-line, that the response time for characterisation of the substance is still too long for accurate control of the flow and that the devices are too expensive and too big for many applications.

DE 41 18 781 describes a device for the characterisation of a gas, in particular for the determination of the Wobbe number and/or heat of combustion of a gas, comprising a pressure control, a lamellar pressure resistance for isothermal expansion of the gas and a mass and a volume flow rate measurement unit. It is described that the gas cools a heating wire with constant over-temperature and the heating power supplied is used as a measure for the mass flow. Apart from that, the volume flow rate is measured. Further, in the device the gas is expanded isothermally over a flow resistance with laminar flow giving rise to a pressure drop. The pressure drop over the flow resistance; the mass and the volume flow measurement unit is measured, which correlates approximately with the density of the gas. The Wobbe number and/or the heat of combustion are evaluated from the measured mass flow, volume flow and pressure drop by substituting the values in an empirical fit-formula, in which the constants are determined by calibration.

EP-A-0469649 describes a calorimeter in which a laminar flow type flow meter for measuring volume flow is put in series with a thermal type flow meter as described above for measuring a mass flow, in which the gas flow is controlled by controlling a constant temperature difference over the sensor and the caloric value of the fuel gas is evaluated from the pressure difference over the volume flow meter. Because this calorimeter requires two flow meters it is rather complex, expensive and bulky. Further, the accuracy and reliability are insufficient.

FR 2818746 describes a process for the evaluation of a Wobbe parameter wherein a combustion gas is compressed and subsequently expanded and wherein on expansion the flow, pressure and temperature characteristics are measured and wherein a reference gas is similarly measured for-determining reference values for accurately evaluating the Wobbe index from an empirical fit formula.

Similarly, in EP-A-0715169 the pressure of a defined volume of gas is raised to a defined pressure level and after that relaxed to the original state, during which relaxation the density and/or the viscosity values are determined, which are input to an empirical fit formula for evaluating the caloric value and/or Wobbe index.

WO 93/08457 and EP 0554095 describe an improved apparatus and methods to derive from multiple measured characteristics of a fuel gas the desired fuel characteristic like for example a Wobbe index.

The problem of the described devices is that they are all relatively complex, expensive and bulky. In particular, it is a disadvantage that the devices are deigned only for the evaluation of heat of combustion of a fuel gas. More importantly, the devices are often too inaccurate and lack reproducibility for more demanding applications.

SUMMARY OF THE INVENTION

There is a desire for a relatively simple, cheap and compact device and a method for a quick but accurate and reliable characterisation of a flowing substance, gas or liquid, that can be used in a flow control device to control the flow rate of an unknown substance. The problem and object of the invention is to provide such a device and method.

This problem is solved according to the invention by a device for the characterisation of a flowing substance comprising:
- a transport duct on which is mounted a heating or a cooling element,
- a temperature difference sensor comprising a first temperature measurement cell downstream of the heating or cooling element and means to determine a temperature difference in the flowing substance upstream and downstream of the heating or cooling element, flow control means comprising flow measurement means for measuring a mass flow characteristic and flow correction means for correcting for measured mass flow variations, and evaluation means for evaluating a characterising feature of the flowing substance comprising a function relating temperature differences measured on one or more calibration substances to one or more characterising features of the flowing substance.

The invention also provides a method for the characterisation of a flowing substance that is relatively simple but accurate. This method comprises the steps of locally heating or cooling the substance flowing through a transport duct, thus creating a temperature difference in the flowing substance upstream and downstream of the heating or cooling element, determining the temperature difference, controlling the flow by measuring a mass flow characteristic and correcting the flow for measured mass flow variations, and comparing the measured temperature difference with corresponding temperature differences measured on calibration substances for evaluating a characterising feature of the flowing substance.

It was found that, in the device and method according to the invention, a very accurate and reproducible temperature difference measurement is obtained and that hence a reliable characterisation can be done.

It is noted that in many publications the term mass flow is inappropriately used. For example in DE 41 18 781 the heating power of the heating element is proportional with the mass flow but also depends on many other factors and cannot be used directly to characterise and control the mass flow of an unknown substance. In the present application mass flow characteristic means, as described in more detail hereafter, a characteristic relating directly to the real mass flow of the unknown flowing substance.

BRIEF DESCRIPTION OF THE DRAWINGS

The following is a description of certain embodiments of the invention given by way of example only and with reference to the appended drawings, in which.

DETAILED DESCRIPTION OF PREFERRED EMBODIMENTS

Figure 1:
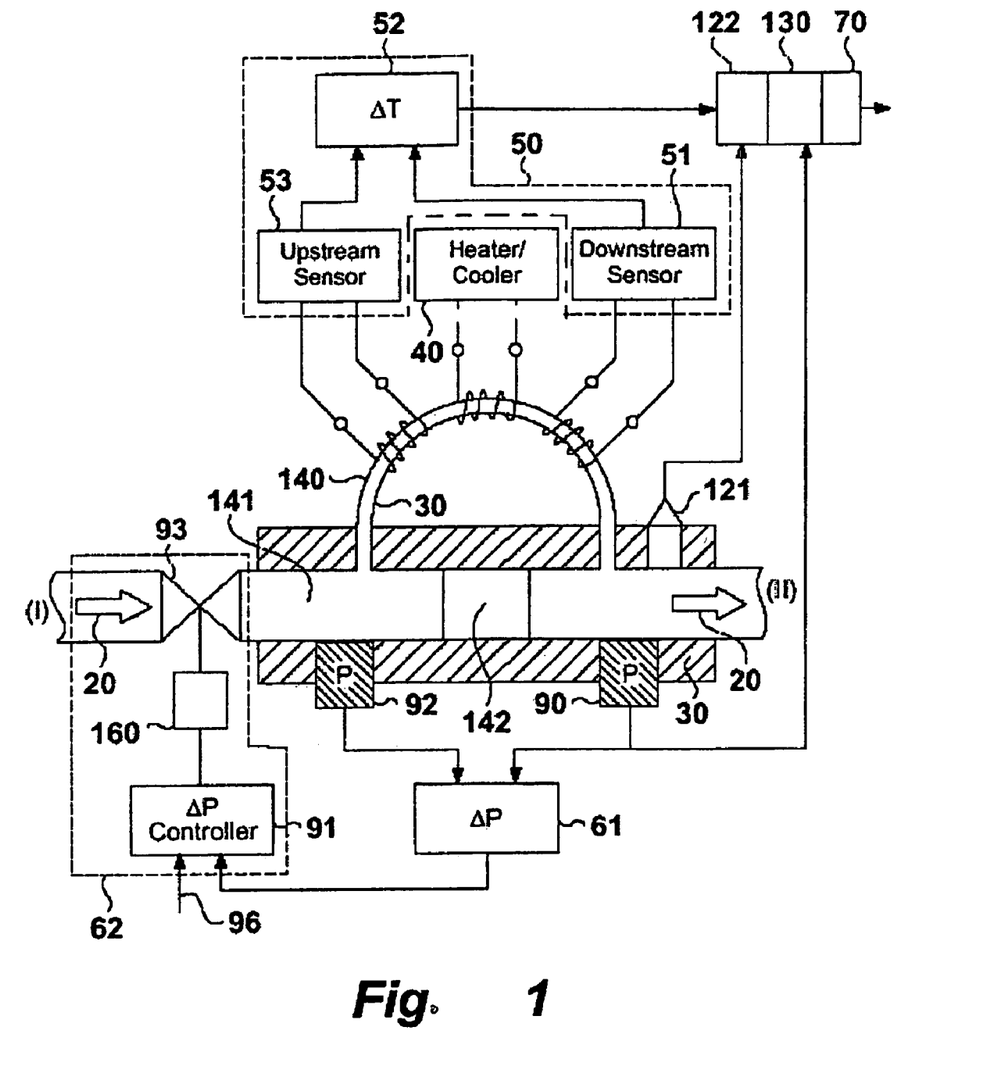
FIG. 1 is a schematic block diagram of one embodiment of the device according to invention including measurement of the pressure difference over the sensor.
Figure 2:
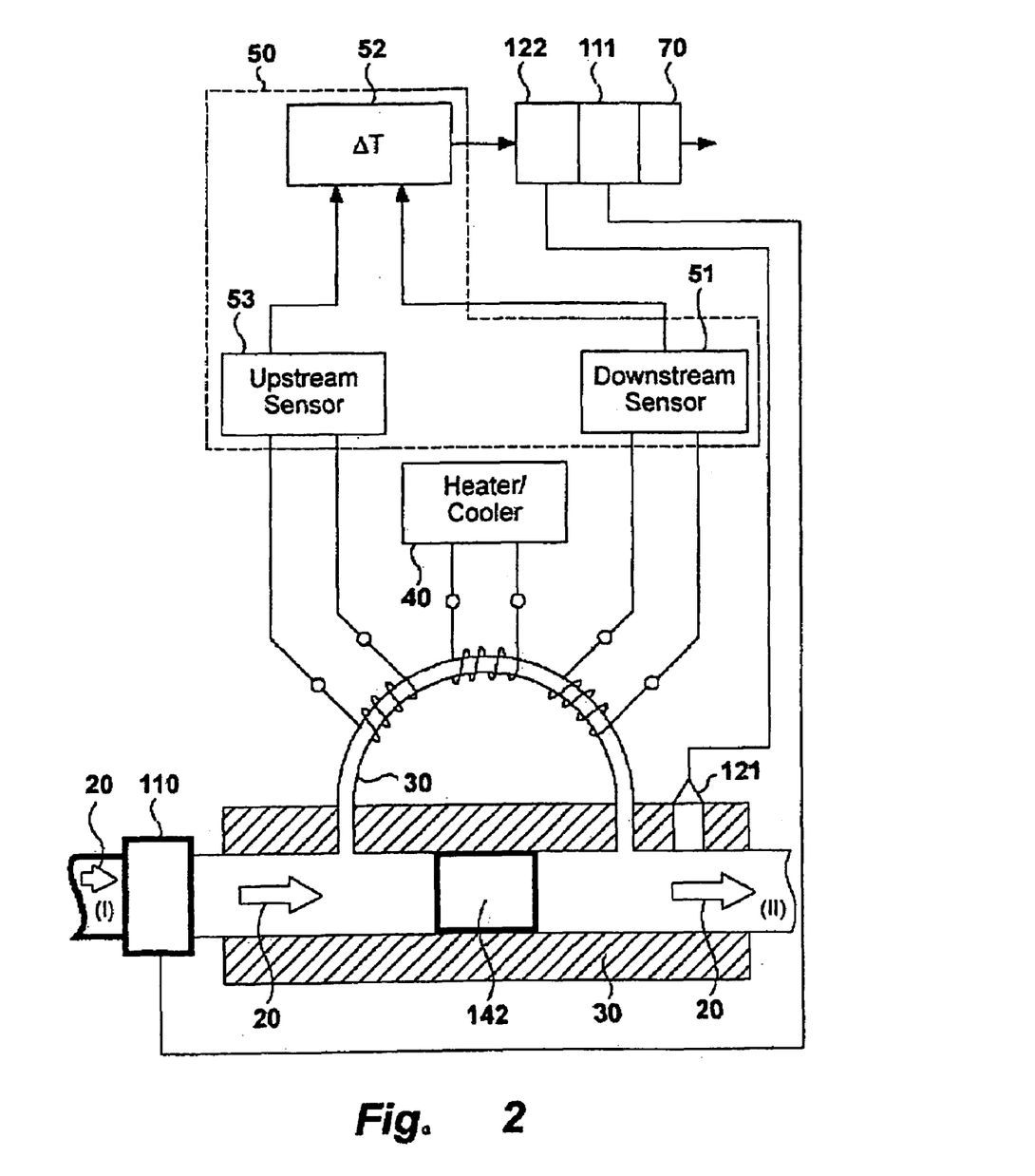
FIG. 2 is a schematic block diagram of another embodiment of the device according to invention including a Coriolis sensor.

The flowing substance is forced to flow through a transport duct (30) on which is mounted a heating or a cooling element (40). The stream before that element is referred to as upstream (indicated I in FIGS. 1 and 2), the stream after the element is referred to as downstream (indicated II in FIGS. 1 and 2). In FIGS. 1 and 2 the flow is forced through the transport duct by a restrictor (142), which can be solid semi-permeable or variable. The heating or cooling element locally heats or cools the substance flowing through a transport duct with an accurately constant amount of heat creating a temperature difference in the flowing substance upstream and downstream of the heating or cooling element.

The temperature difference sensor (50) comprises a first temperature measurement cell (51) downstream of the heating or cooling element. A single downstream measurement cell can be used if the temperature upstream is known from another source and available to the means (52) to determine a temperature difference in the flowing substance upstream and downstream of the heating or cooling element. For accuracy reasons, a second upstream measurement cell (53) is preferred to measure the actual temperature difference. Although in principle good results can be obtained with a cooling element, for example a Peltier element, a heating element is preferred because a cooling element has the risk that gas can condensate on the element. A heating element is more accurate and less expensive. In applications where the flowing medium is a liquid having a boiling point near the measurement temperature, a risk may exists that on heating a phase transition to gas exists. In such cases a Peltier element is preferred.

Devices comprising a heating element and a temperature difference sensor comprising an upstream and downstream temperature measurement cell are known and used as flow controllers, in particular gas flow controllers. Such gas flow controllers are commercially available from Emerson Process Management, Brooks Instrument Division®. The measured temperature difference is proportional to the amount of gas flowing through the sensor and can be used to measure and control the flow.

If, in a given temperature difference measurement sensor, the flow rate of the flowing substance is too high or too low, the accuracy of the temperature difference measurement is too low. Therefore, the device according to the invention preferably also comprises a flow rate means for adjusting flow through the transport duct in a detection range of the temperature difference sensor. The flow rate means can be a valve upstream of the sensor (93) or a variable restrictor (142) in or bridged by the transport duct or a combination of a valve and a restrictor.

The device comprises flow control means comprising flow measurement means (61) for measuring a mass flow characteristic and flow correction means (62) for correcting for measured mass flow variations. The inventors have found that this particular flow control means correcting for real mass flow variations assure an accurate and reproducible temperature difference measurement. The high accuracy and reproducibility assures that the device is capable of identifying substances even if they are very similar and have very close heat capacity.

The flow measurement means (61) can determine the mass flow characteristic directly, by special separate mass flow measurement devices as described below in more detail, or indirectly by measuring the pressure difference over the sensor, preferably at known absolute pressure and temperature. It should be noted that sometimes flow meters or controllers are called mass flow meters/controllers whereas they actually measure/control only volume flow or even just an approximation of the volume flow. The inventors found that using the volume flow control is inadequate for characterising and identification of a flowing medium and gives unreliable results.

Flow correction means (62) can be physical or mathematical. Physical flow correction involves a pressure difference control maintaining a substantially constant pressure difference. Mathematical flow correction involves correcting the measured temperature difference for the influence of measured variations in the mass flow.

The evaluation means (70), for example a computer, use the temperature difference measurement for evaluating a characterising feature of the flowing substance. The evaluation means comprise a function, for example a data-base, a calibration equation or the test of a condition, relating temperature differences measured in defined standard conditions on one or more calibration substances to one or more characterising features of the flowing substance. The evaluation means (70) return the characterising feature as output of the device to the user or to another device. Characterisation of the flowing substance is broadly defined. Depending on the particular application of the device characterisation can be a quantitative measurement of the heat capacity of the substance, the qualitative identification of the substance, ancillary known information of the identified substance or an empirically derived output signal for example for controlling another device.

The function can be a data-base that can be used as a look up table to primarily identify the calibration substance with the best corresponding temperature difference and subsequently return as output one or more characterising features of that calibration substance listed in the database. The database can comprise many different characterising features. It can comprise substance features, for example the heat capacity, the heat of combustion in case of fuels or natural gasses, but also derived features like the name of the substance, the composition of the substance, set-parameters for controlling another device, an address of the supplier of the substance etc.

The function can also be a calibration equation relating the measured temperature difference to a characterising feature. The equation comprises constants determined by measuring the temperature difference on a number of different calibration substances and fitting the results to the known characterising features of the calibration substances. This characterisation directly evaluates a property of the substance without identifying the substance first. The calibration equation can for example relate the measured temperature difference to the specific heat capacity, the Wobbe number of the substance.

The evaluation means can also be used to derive information not directly related to the nature of the substance. In case of changing compositions of known components the evaluation means can evaluate the composition parameters. In application to control burners or engines the resulting output of the evaluation means can be, instead of the heat of combustion or Wobbe number of the gas, just the optimal control set-parameter of a burner or engine. The function is can than be determined quasi empirical by testing optimum performance of the burner for a number of different gasses.

The function can also be the evaluation of a condition, for example comparing the measured temperature difference with a threshold value and returning by the evaluation means a yes or no or an action based on that result.

The function can also be a combination of the aforementioned functions. For example, the evaluation means can determine the heat of combustion by identifying the substance and returning the heat of combustion of the substance. In case the evaluation means cannot give an unambiguous positive identification, the calibration function can give an estimate instead.

The function is defined at known standard measurement conditions in order to get a meaningful evaluation of a characterising feature from a temperature difference measured on an unknown flowing medium. Similarly the calibration substances are measured at standard measurement conditions. Standard measurement conditions are primarily the absolute measurement temperature and pressure. To know the real temperature difference characteristic for the substances, the signal from the temperature measurement cells (53 and 51) should further be calibrated with known substances for the particular apparatus and chosen pressure difference over the temperature difference sensor. The measurement of unknown substances does not necessarily have to be performed at standard conditions if the temperature and pressure are known or sufficiently constant to allow for mathematical correction as explained below.

The flowing substance (20) can in principle be any substance capable of flowing through the transport duct of the sensor, for example a gas, a liquid, an emulsion or dispersion. The preferred mode of construction of the device differs depending on whether the flowing substance is a liquid or a gas.

In a first embodiment of the device, the flow measurement means (61) comprise a pressure measurement cell (90) for measuring a pressure difference over the temperature difference sensor (50) and the flow correction means (62) comprise pressure difference control means (91) for maintaining a substantially constant pressure difference over the temperature difference sensor, for example by operating a valve upstream (93) or downstream of the temperature difference sensor (see FIG. 1). It was found that very accurate and reproducible temperature difference measurements are obtained when the pressure difference over the sensor is maintained substantially constant.

A single pressure measurement cell upstream or downstream of the sensor can in principle be used if the pressure at the other end is known from another source such that the pressure difference in the flowing substance upstream and downstream of the heating or cooling element can be determined. For an accurate characterisation of the flow through the sensor, the pressure should be known directly before and after the temperature difference sensor and hence preferably is measured as close as possible to the sensor. Therefore, a second pressure measurement cell measurement cell (92) is preferred to measure the actual pressure difference. The first and second pressure cell can also be integrated in a single pressure difference measurement cell.

In another embodiment the invention the flow measurement means (61) comprise a pressure measurement cell (90) for measuring a pressure difference over the temperature difference sensor (50) and the flow correction means (62) comprise computing means for mathematically correcting the measured temperature difference for a measured pressure difference variation. The mathematical correction by the flow correction means can be a multiplication of the measured temperature difference by the ratio of the measured pressure difference and the standard pressure difference, that is the pressure difference used for measuring the calibration substances. In view of the accuracy of the temperature difference measurement, the mathematical correction is preferably performed on the basis of a calibration function relating the pressure difference over the sensor to the measured temperature difference. Preferably, the absolute temperature and absolute pressure are substantially the same as in the calibration measurements.

In another embodiment the flow measurement means (61) comprise a mass flow sensor (110) measuring the mass flow through the temperature difference sensor (50) and the flow correction means (62) comprise mass flow control means (91) for maintaining a substantially constant mass flow through the temperature difference sensor (50). In an alternative embodiment (shown in FIG. 2), the flow correction means (62) comprises computing means (111) for mathematically correcting the measured temperature difference for a measured mass flow variation. The mathematical correction of the mass flow variation with respect to the standard measurement condition is done as described above.

Suitable mass flow sensors (110) are, for example, a coriolis-, an ultrasonic or a sonic nozzle mass flow sensor. Mass flow sensors directly measure mass flow, irrespective of pressure difference variations over the sensor and absolute temperature and pressure differences. A mass flow sensor allows for more accurate control of the mass flow through the sensor and accurate and reproducible temperature difference measurement. This embodiment, using Coriolis mass flow measurement, is particularly suitable for characterising fluids. A further advantage of using the mass flow sensors described above is that they as a result of the same measurement also produce the density of the flowing medium which can be used as additional information by the evaluation means (70) to identify or characterise the flowing medium. The resolution of the identification, that is the chance of uniquely identifying an unknown compound in a set of (similar) compounds, increases by looking in the calibration substances database for the closest match in both the measured temperature difference and the density.

In an open-ended system, changes in atmospheric pressure can cause significant changes in the downstream absolute pressure. Keeping the pressure difference over the sensor constant, as in one embodiment of the invention, does not (necessarily) result in a constant absolute pressure in the sensor. In case of liquids the effect of absolute pressure deviations are small. In case the flowing substance is a gas correction is however preferred. To further improve the reproducibility, the device according to the invention preferably comprises pressure correction means to correct for an absolute pressure variation in the flowing substance.

The correction preferably is physical because that gives more accurate results. The correction means comprise a pressure control for maintaining a substantially constant absolute pressure in the flowing substance, for example by including a valve up- and down stream and a separate control for maintaining a substantially constant absolute pressure. Mathematical correction can be applied here as well. Mathematical correction of the absolute temperature or pressure has the advantage that the device is simpler and cheaper.

Preferably the device also comprises temperature correction means to correct for an absolute temperature variation in the flowing substance. The correction can be physical, for example by a thermo stated housing, or mathematical by temperature correction means comprising temperature measurement means (121) and calculation means (122) for mathematical correction of the measured temperature difference over the sensor (50) for a measured absolute temperature variation.

In a preferred embodiment, the flow measurement means (61) comprise a pressure measurement cell (90) for measuring a pressure difference over the temperature difference sensor (50) and the device further comprises temperature correction means to correct for an absolute temperature variation in the flowing substance and pressure correction means to correct for absolute pressure variations in the flowing substance. The advantage is that this device shows a more accurate and very reproducible temperature difference measurement. A schematic representation of a preferred embodiment is illustrated in FIG. 1, the device comprises an upstream (92) and a downstream pressure cell (90) of the pressure difference measurement, wherein the downstream pressure cell is used also to determine absolute downstream pressure for input to the mathematical correction means. The pressure difference is input to physical flow control means (62) comprising a pressure difference controller operating a valve (93) to maintain substantially constant pressure difference over the temperature sensor (50). Further, in FIG. 1 a temperature measurement means (121) determines the absolute downstream temperature for input in calculation means (122) for correction of the absolute temperature variations.

In case the flowing substance is a gas, mathematical correction for deviations in absolute pressure and temperature from the standard conditions can in a first approximation be calculated from a general formula based on the ideal gas behaviour of gasses. The corrected temperature difference value ($\Delta T_{meas}$) is obtained by multiplying the measured temperature difference ($\Delta T_{meas}$) by a correction factor ($Q_T$) for absolute temperature deviations ($T-T_{stand}$) and by a correction factor ($Q_P$) for absolute pressure deviations ($P-P_{stand}$). $Q_T$ and $Q_P$ are 1 in case the device has physical correction for absolute temperature or pressure.

$\Delta T_{corr}$ can be calculated as follows:

$$\Delta T_{corr} = \Delta T_{meas} * Q_T * Q_P$$

Wherein:

$$Q_T = 1 + (T-T_{stand})/(273+T_{stand}) + 0.00286*(T-T_{stand})$$

$$Q_P = P_{stand}/P \ (P \text{ in mbar})$$

Preferably, the mathematical correction can be done on the basis of a calibration determined by measuring the absolute temperature or pressure dependence of the temperature difference measurement on calibration substances that are similar to the unknown flowing substances expected. This can be done in a meaningful way for well-defined application areas, where the general nature of the flowing substances is known as for example, in characterising unknown natural gasses. The absolute temperature and pressure dependence can be determined on a set of different natural calibration gasses to establish the range and average of the corrections factors to be applied.

Typically, the transport duct (30) is mounted as a by-pass (140) on a main duct (141) in which a part of the substance flows from the main duct through the transport duct and sensor and back into the main duct. To create the flow through the by-pass a restrictor element (142) can be integrated in the main duct creating a pressure difference over the temperature difference sensor. The restrictor element can for example be a valve, a duct element with a smaller cross-section area or a porous substance.

In a special embodiment the device comprises a switch (160) for switching on and off the flow control means. In the on-mode the pressure controller is used according to the invention to control a constant pressure difference over the sensor for characterisation of the flowing medium. In the off-position, the actual flow rate of the flowing substance through the transport duct is measured, now using the measured temperature difference and/or using the pressure difference over the sensor as a measure for the mass flow. The flow rate can also be controlled to a constant set value (96) by the same pressure controller (91) that controls the pressure difference over the sensor by operating valve (93). The advantage is that the device is more versatile because it can perform as flow controller and for characterising a substance.

Another preferred embodiment comprises means for intermittently switching the switch to the on- and the off position and means to control the flow rate of the flowing substance in the off-position of the switch at a level determined by a characterising feature of the flowing substance determined in the on-position of the switch. The advantage of this intelligent device is that it can control the flow depending on the characterising feature or nature of the flowing substance. For example, the device in the on-mode identifies the gas, retrieves from the database the heat of combustion of the gas, then determines the flow rate required for delivering a constant heat of combustion according to a given preset level. This device is particularly useful for controlling the flow of a fuel of varying origins and compositions to combustion engines or ovens.

The device according to the invention may be used for the identification of a flowing substance, in particular natural gasses, or for controlling the flow of a fuel to deliver a controlled heat of combustion, for example to an engine or to a burner, as an analytical instrument for the determination of the heat capacity of a flowing substance or, for example in environmental protection and control, for the identification of the origin, source or supplier of a flowing substance. An engine comprising a device for controlling fuel has the advantage of being able to optimally combust the fuel even when the composition varies from time to time. The device and method of the invention can be used also to detect air pollution. The database can then be adapted to enable identification of the source and nature of the pollution.

A method for the characterisation of a flowing substance may comprise the steps of:
Locally heating or cooling a substance flowing through a transport duct by a heating or cooling element,
Determining a temperature difference in the flowing substance upstream and downstream of the heating or cooling element,
Controlling mass flow of the flowing substance in the transport duct by measuring a mass flow characteristic and correcting for measured variations in the mass flow characteristic, and
comparing the measured temperature difference with corresponding temperature differences measured on calibration substances for evaluating a characterising feature of the flowing substance.

Detailed explanation of preferences and advantages described above for the device correspondingly apply where appropriate to the methods described above.

The method can be carried out in many different embodiments. In one embodiment of the method the measured mass flow characteristic is a pressure difference over the heating- or cooling element and the measured temperature difference is corrected mathematically for a measured pressure difference variation. The advantage of this embodiment is that it is simple and cheap to produce, whilst giving sufficiently accurate temperature difference measurement and characterisation of the flowing substance for many purposes and applications.

In another embodiment of the method the measured mass flow characteristic is a pressure difference over the heating- or cooling element and the mass flow is corrected for a measured pressure difference variation to maintain a substantially constant pressure difference over the element. The advantage of this embodiment is that the physical correction gives more accurate and reproducible temperature difference measurements and hence more reliable characterisation of the flowing substance.

For more critical applications, where a high reproducibility and accuracy of the temperature difference measurement is required preferably further correction is made for absolute temperature variations and absolute pressure variations in the flowing substance in a way described above. In a preferred embodiment, wherein the measured mass flow characteristic is a pressure difference over the heating- or cooling element, the mass flow is corrected for the measured pressure difference variation to maintain a substantially constant pressure difference over the element and correction is made for absolute temperature variations and absolute pressure variations in the flowing substance.

In a different embodiment of the method the measured mass flow characteristic is the real mass flow rate in the transport duct measured with a mass flow sensor and physically corrected to maintain a substantially constant mass flow rate. The advantage of this embodiment is that the temperature difference measurement is very accurate and reproducible. Suitable mass flow sensors and their applications are described above.

In a more simple and cheaper but still very accurate and reproducible embodiment of the method the measured mass flow characteristic is a real mass flow rate in the transport duct measured with a mass flow sensor and the measured temperature difference is mathematically corrected for a measured mass flow rate variation.

Figure 3:
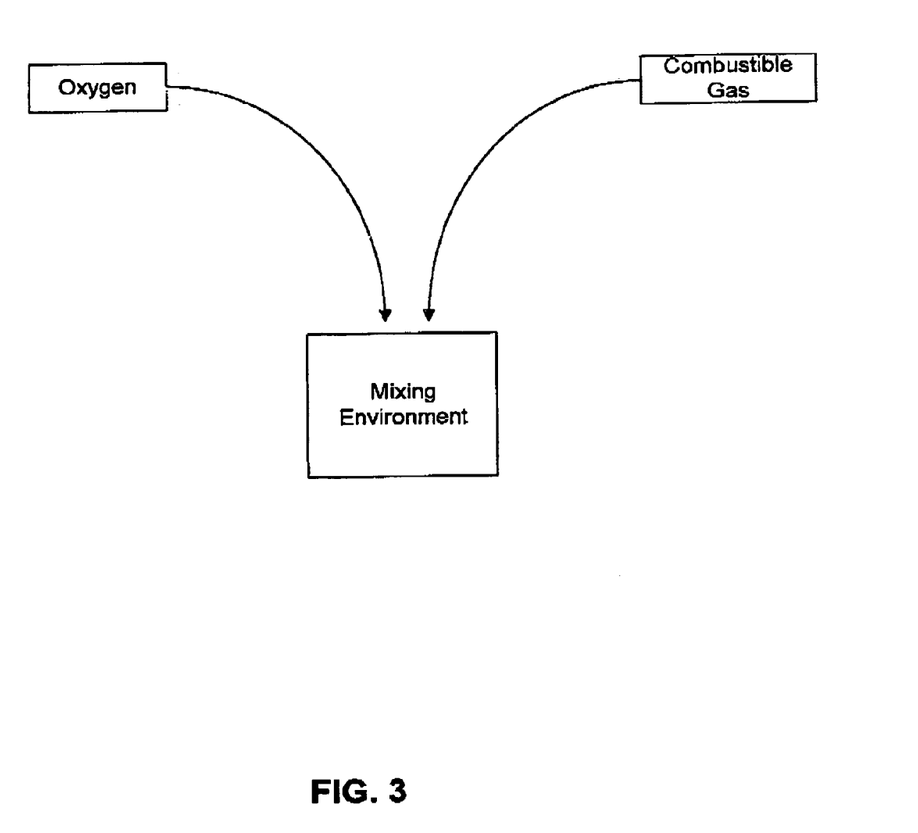
FIG. 3 is a block diagram of oxygen and a combustible gas mixing in accordance with an illustrative embodiment.

In the method the flowing substance is identified by retrieving from a database the identity of the calibration substance with the best corresponding temperature difference measurement. Once the flowing substance is identified the known properties of that substance can be returned to the user. In an important application of the method the flowing substance is a natural gas and the natural gas is characterised by measuring the temperature difference and retrieving from a database or function, relating temperature difference measurements of different natural gasses with one or more characterising features of said natural gasses, the characterising feature relating to the measured temperature difference measurement. For example, in the method the database or function comprises the heat of combustion of calibration gasses and the temperature difference measurement is used to determine the heat of combustion of the gas. This principle can be used in a method for the combustion of a combustion gas wherein the combustion gas is characterised according to the method of the invention and mixed with an oxygen containing gas in a mixing ratio based on the measured temperature difference as shown in FIG. 3.

The combustion gas can be natural gas, bio-gas or industrial waste gasses, but also the vaporised fuel of combustion engines.

Thus, the invention has been described by reference to certain embodiments. It will be recognised that these embodiments are susceptible to many modifications and alternative forms well known to those of skill in the art. Accordingly, although specific embodiments have been described, these are examples only and are not limiting on the scope of the invention.

The invention claimed is:
1. A device for the characterisation of a flowing substance (20) comprising:
a transport duct (30) on which is mounted a heating or a cooling element (40),
a temperature difference sensor (50) comprising a first temperature measurement cell (51) downstream of the heating or cooling element and means (52) to determine a temperature difference in the flowing substance upstream and downstream of the heating or cooling element,
flow control means comprising flow measurement means (61) for measuring a mass flow characteristic and flow correction means (62) for correcting for measured mass flow variations, and evaluation means (70) for evaluating a characterising feature of the flowing substance comprising a function relating temperature differences measured on one or more calibration substances to one or more characterising features of the flowing substance.

2. The device according to claim 1, wherein the function comprises a data-base or a calibration equation.

3. The device according to claim 1, further comprising a flow rate means for adjusting flow through the transport duct in a detection range of the temperature difference sensor.

4. The device according to claim 3, wherein the flow measurement means (61) comprises a pressure measurement cell (90) for measuring a pressure difference over the temperature difference sensor (50) and the flow correction means (62) comprises a pressure difference control means (91) for maintaining a substantially constant pressure difference over the temperature difference sensor.

5. The device according to claim 3, wherein the flow measurement means (61) comprises a pressure measurement cell (90) for measuring a pressure difference over the temperature difference sensor(50) and the flow correction means (62) comprises a computing means for mathematically correcting the measured temperature difference for a measured pressure difference variation.

6. The device according to claim 3, wherein the flow measurement means (61) comprises a mass flow sensor (110) measuring the mass flow through the temperature difference sensor (50) and the flow correction means (62) comprises a mass flow control means (91) for maintaining a substantially constant mass flow through the temperature difference sensor (50).

7. The device according to claim 3, wherein the flow measurement means (61) comprises a mass flow sensor (110) measuring the mass flow through the sensor (50) and the flow correction means (62) comprises a computing means (111) for mathematically correcting the measured temperature difference for a measured mass flow variation.

8. The device according to claim 3, wherein the flow measurement means (61) comprises a pressure measurement cell (90) for measuring a pressure difference over the temperature difference sensor (50), and further comprising a temperature correction means to correct for an absolute temperature variation in the flowing substance and a pressure correction means to correct for absolute pressure variations in the flowing substance.

9. The device according to claim 1, wherein the flow measurement means (61) comprises a pressure measurement cell (90) for measuring a pressure difference over the temperature difference sensor (50) and the flow correction means (62) comprises a pressure difference control means (91) for maintaining a substantially constant pressure difference over the temperature difference sensor.

10. The device according to claim 9, further comprising a temperature correction means to correct for an absolute temperature variation in the flowing substance and a pressure correction means to correct for absolute pressure variations in the flowing substance.

11. The device according to claim 1, wherein the flow measurement means (61) comprises a pressure measurement cell (90) for measuring a pressure difference over the temperature difference sensor (50) and the flow correction means (62) comprises a computing means for mathematically correcting the measured temperature difference for a measured temperature difference variation.

12. The device according to claim 11, further comprising a temperature correction means to correct for an absolute temperature variation in the flowing substance and a pressure correction means to correct for absolute pressure variations in the flowing substance.

13. The device according to claim 1, wherein the flow measurement means(61) comprises a mass flow sensor (110) measuring the mass flow though the temperature difference sensor (50) and the flow correction means (62) comprises a mass flow control means (91) for maintaining a substantially constant mass flow through the temperature difference sensor (50).

14. The device according to claim 13, wherein the mass flow sensor (110) comprises a coriolis, an ultrasonic or a sonic nozzle mass flow sensor.

15. The device according to claim 1, further comprising a temperature correction means to correct for an absolute temperature variation in the flowing substance.

16. The device according to claim 15, wherein the temperature correction means comprises a temperature measurement means and a calculation means (122) for mathematical correction of the measured temperature difference over the sensor (50) for a measured absolute temperature variation.

17. The device according to claim 1, further comprising a pressure correction means to correct for an absolute pressure variation in the flowing substance.

18. The device according to claim 17, wherein the pressure correction means comprises a pressure control for maintaining a substantially constant absolute pressure in the flowing substance.

19. The device according to claim 1, wherein the flow measurement means (61) comprises a pressure measurement cell (90) for measuring a pressure difference over the temperature difference sensor (50), and further comprising a temperature correction means to correct for an absolute temperature variation in the flowing substance and a pressure correction means to correct for absolute pressure variations in the flowing substance.

20. The device according to claim 1, wherein the transport duct (30) is mounted as a by-pass (140) on a main duct(141) in which a part of the substance flows from the main duct through the transport duct and sensor and back into the main duct.

21. The device according to claim 1, further comprising a switch (160) for switching on and off the flow control means, wherein, in an off-position, the device measures a flow rate of the flowing substance through the transport duct.

22. The device according to claim 21, comprising a means for intermittently switching the switch to the on- and the off position and a means to control the flow rate of the flowing substance in the off-position of the switch at a level determined by a characterising feature of the flowing substance determined in the on-position of the switch.

23. A method of use of the device according to claim 1, comprising:
flowing a substance through the device of claim 1; and
identifying the flowing substance.

24. A method of use of a device according to claim 1, comprising:
flowing a fuel substance through the device of claim 1; and
controlling the flow of the fuel substance to deliver a controlled heat of combustion.

25. A method of use of a device according to claim 1, comprising:
flowing a substance through the device of claim 1; and
determining a heat capacity of the flowing substance.

26. A method of use of a device according to claim 1, comprising:
- flowing a substance through the device of claim 1; and
- identifying a source or supplier of the flowing substance.

27. A device for the characterisation of a flowing substance (20) comprising:
- a transport duct (30) on which is mounted a heating or a cooling element (40):
- a temperature difference sensor (50) comprising a first temperature measurement cell (51) downstream of the heating or cooling element and means (52) to determine a temperature difference in the flowing substance upstream and downstream of the heating or cooling element;
- flow control means comprising flow measurement means (61) for measuring a mass flow characteristic and flow correction means (62) for correcting for measured mass flow variations;
- evaluation means (70) for evaluating a characterising feature of the flowing substance comprising a function relating temperature differences measured on one or more calibration substances to one or more characterising features of the flowing substance; and
- the flow measurement means (61) comprises a mass flow sensor (110) for measuring the mass flow through the sensor (50) and the flow correction means (62) comprises a computing means (111) for mathematically correcting the measured temperature difference for a measured mass flow variation.

28. The device according to claim 27, wherein the mass flow sensor (110) comprises a coriolis, an ultrasonic or a sonic nozzle mass flow sensor.

29. A method for the characterisation of a flowing substance comprising:
- locally heating or cooling a substance flowing through a transport duct by a heating or cooling element,
- determining a temperature difference in the flowing substance upstream and downstream of the heating or cooling element,
- controlling mass flow of the flowing substance in the transport duct by measuring a mass flow characteristic and correcting for measured variations in the mass flow characteristic, and
- comparing the measured temperature difference with corresponding temperature differences measured on one or more calibration substances for evaluating a characterising feature of the flowing substance.

30. The method according to claim 29, wherein the measured mass flow characteristic comprises a pressure difference over the heating-or cooling element and further comprising correcting the mass flow for a measured pressure difference variation to maintain a substantially constant pressure difference over the element.

31. The method according to claim 29, wherein the measured mass flow characteristic comprises a pressure difference over the heating-or cooling element and further comprising correcting mathematically the measured temperature difference for a measured pressure difference variation.

32. The method according to claim 29, wherein the measured mass flow characteristic comprises a real mass flow rate in the transport duct measured with a mass flow sensor and further comprising correcting the mass flow rate for a measured mass flow rate variation to maintain a substantially constant mass flow rate.

33. The method according to claim 29, wherein the measured mass flow characteristic comprises a real mass flow rate in the transport duct measured with a mass flow sensor and further comprising correcting mathematically the measured temperature difference for a measured mass flow rate variation.

34. The method according to claim 29, wherein the measured mass flow characteristic comprises a pressure difference over the heating-or cooling element and further comprising correcting the mass flow rate for the measured pressure difference variation to maintain a substantially constant pressure difference over the element, and correcting for absolute temperature variations and absolute pressure variations in the flowing substance.

35. The method according to claim 29, further comprising identifying the flowing substance by retrieving from a database the identity of the calibration substance with the best corresponding temperature difference measurement.

36. The method according to claim 29, wherein the flowing substance is a natural gas and further comprising:
- characterising the natural gas by measuring the temperature difference; and
- retrieving from a database or function, relating temperature difference measurements of different natural gasses with one or more characterising features of said natural gasses.

37. The method according to claim 36, wherein the database or function comprises the heat of combustion of calibration gasses and further comprising using the temperature difference measurement to determine the heat of combustion of the gas.

38. A method for a combustion of a combustion gas, comprising:
- characterizing the combustion gas according to method claim 37; and
- mixing the combustion gas with an oxygen containing gas in a mixing ratio based on the measured temperature difference for the combustion.

* * * * *